United States Patent [19]

Armstrong

[11] 4,416,625

[45] Nov. 22, 1983

[54] ORTHODONTIC SPRING FORCE ADJUSTMENT AND DISCONNECTIBLE CONNECTION

[75] Inventor: Maclay M. Armstrong, Seattle, Wash.

[73] Assignee: Northwest Orthodontics, Inc., Seattle, Wash.

[21] Appl. No.: 124,842

[22] Filed: Feb. 26, 1980

Related U.S. Application Data

[63] Continuation-in-part of Ser. No. 33,111, Apr. 25, 1979, Pat. No. 4,368,039, which is a continuation-in-part of Ser. No. 655,401, Feb. 5, 1976, Pat. No. 4,155,161, which is a continuation-in-part of Ser. No. 613,243, Sep. 15, 1975, abandoned.

[51] Int. Cl.³ .................................................. A61C 7/00
[52] U.S. Cl. ........................................................ 433/5
[58] Field of Search ........................................ 433/6, 5

[56] References Cited

U.S. PATENT DOCUMENTS 4,167,061  9/1979  Förster .................................... 433/5
4,259,065  3/1981  DeWoskin .............................. 433/5

Primary Examiner—Robert Peshock
Attorney, Agent, or Firm—Robert W. Beach; Ward Brown

[57] ABSTRACT

An extraoral force-reaction device engageable with the wearer's head and/or neck, such as a headcap or a neckband, is connected to an intraoral force-applying device, such as molar bands, by helical spring force-producing means. Snapback of the force-applying means is controlled in response to stressing of the force-producing means beyond a predetermined maximum degree of force exerted by the force-producing means. Snapback control is effected by disconnectible connection means which can be disconnected to interrupt the application to the intraoral means of force capable of moving such intraoral means. The force to be exerted by the spring force-producing means can be readily adjustable in predetermined increments, such as by engaging a spring end hook selectively with any anchor post of several posts arranged in a row lengthwise of the spring.

13 Claims, 18 Drawing Figures

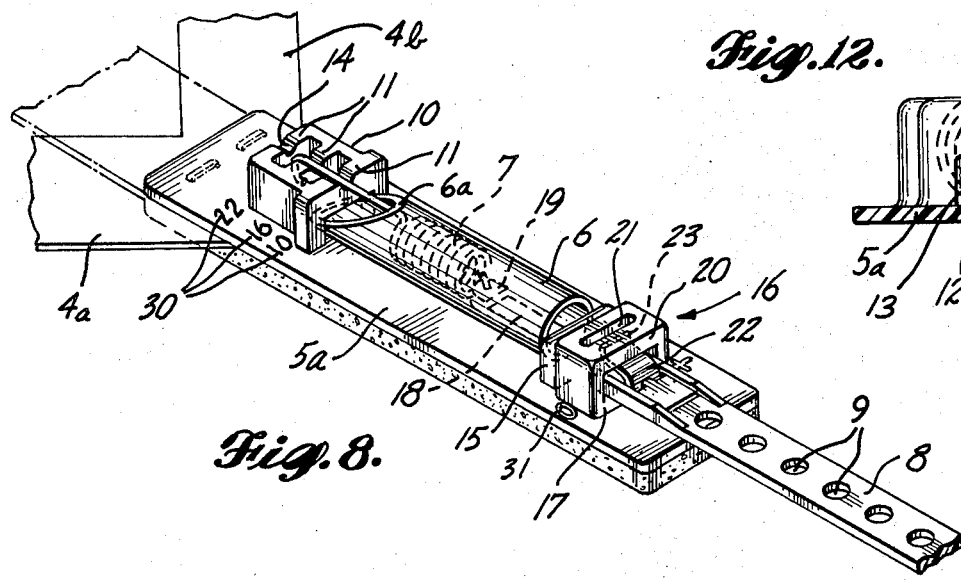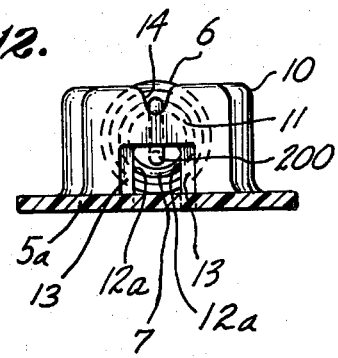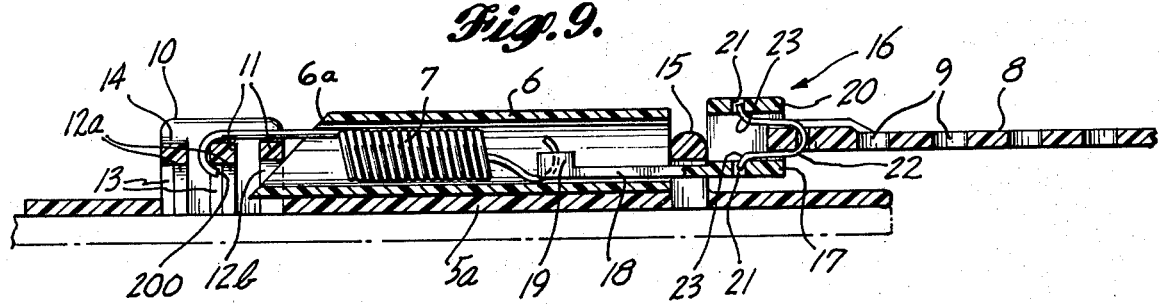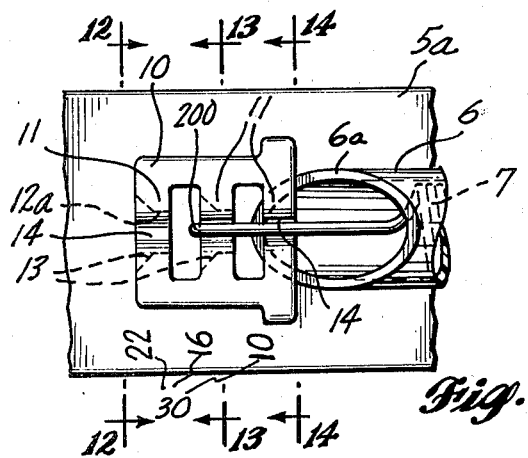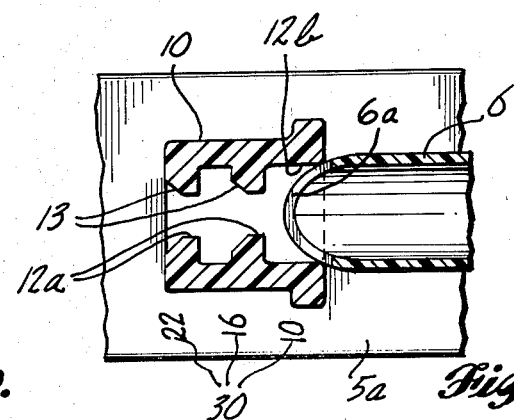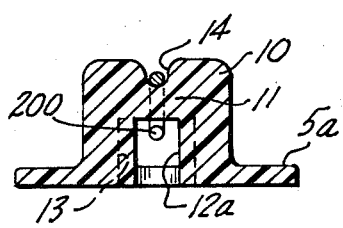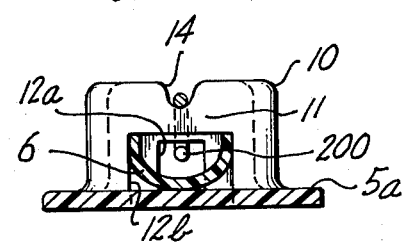

ORTHODONTIC SPRING FORCE ADJUSTMENT AND DISCONNECTIBLE CONNECTION

CROSS-REFERENCE

This application is a continuation-in-part of my application Ser. No. 33,111, filed Apr. 25, 1979 now U.S. Pat. No. 4,368,039, for Disconnect for Neckstrap or Headcap Reaction Member, which was a continuation-in-part of my application Ser. No. 655,401, filed Feb. 5, 1976, now U.S. Pat. No. 4,155,161, for Extraoral Force-Applying Orthodontic Appliance, which was a continuation-in-part of my application Ser. No. 613,243, filed Sept. 15, 1975 and now abandoned, for Extraoral Force-Applying Orthodontic Appliance.

BACKGROUND OF THE INVENTION

1. Field of the Invention

This application relates to orthodontic appliances capable of applying a primary force to a jaw, the reaction from which force is applied to the exterior of the head and/or neck by an extraoral force-reaction device.

2. Prior Art

A device for applying primary force to a jaw by an intraoral device and exerting the reaction force on an extraoral force-reaction device engageable with the wearer's head and/or neck is shown, for example, in the Armstrong U.S. Pat. Nos. 3,526,035 and 4,115,921. The appliance of the present invention constitutes an improvement over the apparatus shown in those patents.

The Problem

The problem which until recently has not been solved by prior orthodontic devices has been provision of protection against injury should the intraoral device remain connected to the force-reaction component, such as a headcap and/or neckband, if the intraoral device is pulled from the patient's mouth. Such injury could occur by childish pranks, or by a part of the headgear being caught by either a stationary or a moving object. One solution to this problem was proposed in my U.S. Pat. No. 4,115,921; however, the disconnectible connection of the present invention is more compact and more economical to manufacture.

Another problem has been provision of a means to enable the orthodontist to quickly and precisely adjust the amount of force to be applied to a jaw. While ease in adjustment by the orthodontist is desirable, preferably alteration of the adjustment by the patient should be deterred.

SUMMARY OF THE INVENTION

A principal object of the present invention is to provide, in an orthodontic appliance having extraoral force-reaction and intraoral force-applying components, a force-producing unit which will produce a sustained, substantially constant, predetermined force on a jaw, such as by a preliminarily stressed spring, which force-producing unit can be adjusted quickly and easily to produce different predetermined degrees of force while having a restricted range of movement for any selected predetermined force.

A further object is to provide such an easily adjusted force-producing unit which will deter alteration of the adjustment by the patient.

It is a further object to provide an improved disconnectible connection between extraoral force-reaction gear and intraoral force-applying gear which is very precise and which will be disconnected immediately if a predetermined force which it is set to withstand is exceeded only slightly, and which gear components can be disconnected by a small amount of relative movement. Such disconnection will occur whenever the extraoral force-reaction gear is pulled excessively, whether intentionally or inadvertently, or is merely caught and the wearer exerts the force exceeding the predetermined force.

If the gear components are disconnected, it is an object to enable the gear to be rearranged or restored to its operative condition quickly and easily.

It is also an object to provide orthodontic gear having the foregoing capabilities which is light, compact, durable, of simple and economical construction and which can be fitted quickly, easily and accurately to the patient.

The foregoing objects can be accomplished by orthodontic gear including intraoral force-applying and extraoral force-reaction components connected by a component connector including a force-producing spring component which normally is yieldable relative to either the intraoral force-applying component or the extraoral force-reaction component, which can be adjusted to a preselected degree of force, and which can be freed from the extraoral component by an improved, more compact, disconnectible connection component.

BRIEF DESCRIPTION OF THE DRAWINGS

FIGS. 4, 5, 6 and 7 are fragmentary top perspectives corresponding to FIG. 3 showing modified spring force adjustments.

FIG. 8 is a top perspective of a component connector including an improved spring force adjustment, spring housing and disconnnectible connection component, having parts broken away.

FIG. 9 is a longitudinal section through the component connector on an enlarged scale.

FIG. 10 is a plan of the spring force adjustment, on a further enlarged scale and having parts broken away.

FIG. 11 is a horizontal section through the spring force adjustment of FIG. 10 with the spring omitted.

FIGS. 12, 13 and 14 are sections taken along lines 12—12, 13—13 and 14—14 in FIG. 10, respectively.

DETAILED DESCRIPTION

Figure 1:
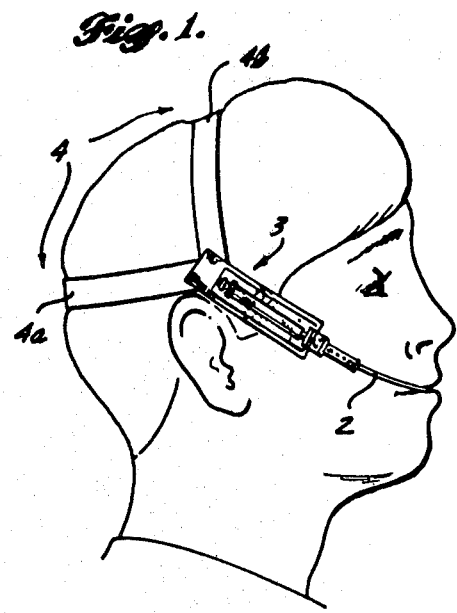
FIG. 1 is a side elevational of a patient shown wearing one type of orthodontic appliance to which the present invention pertains.
Figure 3:
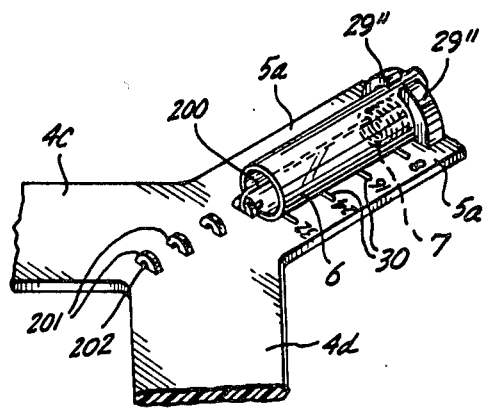
FIG. 3 is a fragmentary top perspective of a portion of such headgear showing a spring force adjustment.

Orthodontic headgear includes an extraoral force-reaction component engageable with the wearer's head and/or neck, a force-applying component, such as an intraoral component, by which force is applied to a jaw, and connectors, each having a force-producing unit, connecting the opposite sides of such components for producing a sustained force applied to the force-applying component. The term "intraoral" as used in the following description and claims is intended to include force-applying devices for orthodontic treatment which contact the exterior of the lower jaw, such as a chin cup, as well as devices received in the mouth. The representative type of headgear illustrated in FIG. 1 has an extraoral force-reaction component or headcap 4, but such component could be a neckband as shown in FIG. 1 of U.S. Pat. No. 4,115,921, or a combination headcap and neckband as shown in FIG. 3 of that patent.

The headcap 4 is composed of a lower band 4a extending around the back of the head and an upper band 4b extending across the top of the head. The ends of these bands are connected together and to the rearward end of the force-producing connector unit 3. A tie rod 2 is connected to the intraoral component and the force-producing connector unit 3. The force produced by the force-producing unit 3 applies a pull on the tie rod 2, which exerts a corresponding rearward and upward force on the intraoral, or force-applying, component of the headgear to which the tie rod 2 is connected.

It is desirable for the force-producing units to be constructed for easy substitution in the gear or for easy adjustment to produce different degrees of force. Also it is desirable to enable the various components of the headgear to be connected readily and disconnected at will or automatically in response to relative displacement of components more than a predetermined amount.

Figure 2:
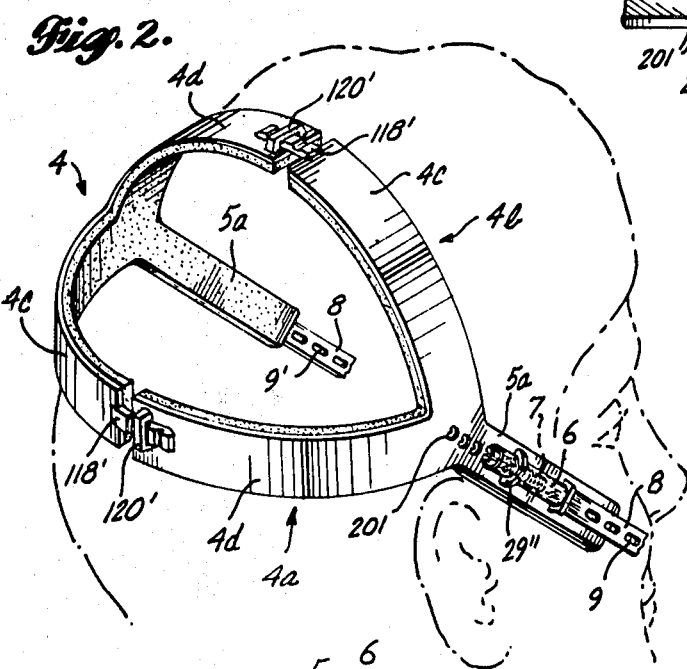
FIG. 2 is a top rear perspective of a somewhat different type of headgear showing a headcap incorporating the spring force adjustment of the present invention.

The principal features of the invention can be incorporated in a connector which connects an extraoral force-reaction band member, such as a headcap band structure 4a, 4b, with a tie rod 2, by which the pulling force is applied to intraoral force-applying gear. FIG. 2 shows one type of connector which includes a force-producing unit having a backing 5a that can be attached suitably to the reaction force band component by being bonded to such component. FIG. 8 shows such a backing 5a stapled to a reaction force band component 4a, 4b. Preferably the force-producing helical spring 7 carried by the backing 5a is enclosed in a housing tube 6. Such tube, shown in FIG. 2, is held in place on the backing by posts 29" integral with the backing which curve upward toward each other over the tube. The helical tension spring 7 is slidable within the housing tube 6. The force-producing unit can be connected to the tie rod 2 by a side strap 8, having apertures 9 at regularly spaced intervals along its length for engagement by a hook on the end of the tie rod. The purpose of having a plurality of apertures in the strap is to enable the tie rod hook to be engaged in the appropriate aperture so that the proper length of connection between the force-producing unit and the tie rod for the particular patient can be selected.

With the parts of the orthodontic appliance in the normal treating relationship of FIGS. 1 and 2, the spring 7 of the force-producing unit would exert a sustained and substantially uniform force on the tie rod 2 directed inwardly and upwardly. It may be desirable to alter the force applied to the tie rod for treating different orthodontic conditions. While the spring 7 could be preliminarily stressed to produce substantially a predetermined force for application to the intraoral device, so that the force produced could be altered by selecting different preliminarily stressed springs, the force-producing unit 3 shown in the appliance of FIGS. 3 to 7 can be adjusted so as to produce different degrees of force.

To provide for selective adjustment of the spring 7 by increments over a considerable range of selectible average treatment forces, the end of spring 7 remote from the tie rod is attached to one of a plurality of anchors. The anchors are spaced along the length of backing 5a in a row aligned with the spring and at distances corresponding to increments of force, for which force increments the stress of and force produced by spring 7 can be altered without changing appreciably the variation in force which occurs as a result of relative movement of the tie rod 2 and the force-producing unit 3 during normal use of the gear. The spring 7 has been stressed to the extent necessary for the spring to produce the desired degree of orthodontic treatment force which is applied to the intraoral component of the appliance. The hooked free end 200 of the spring 7 is then anchored.

The initial stress of the spring 7 within the tube 6 can be adjusted to alter the force exerted by the force-producing unit on the force-applying device. As shown in FIG. 2, the tube enclosing the spring is held on the backing 5a by being lodged between posts 29" upstanding from the backing at opposite sides of the tube. One end of the helical spring 7 is connected to the side strap 8, and the other end of such spring can be anchored to the force-reaction portion of the headgear at any selected one of a number of different locations.

Different types of spring end anchor structures are shown in detail in FIGS. 3 to 7. In each instance, the anchoring structure is engaged by a wire hook 200 connected to one end of the spring 7. Each form of the spring-anchoring means includes hook-engageable anchor members spaced axially of the tube 6 and spring 7.

In the form of anchoring means shown in FIG. 3, the hook-engageable members are curved arches 201 having curved passages 202 extending through them in which the spring-anchoring hook 200 can be engaged.

In FIG. 4, the hook-engageable arches 203 are square and have square passages 204 extending through them. With this type of construction, the hook 200 can be engaged either with the top of the arch or with either side of the arch. In each instance, the hook shank will extend alongside the inner surface of the tube 6 instead of extending generally centrally through the tube. The hook shank should be long enough so that the spring will be housed completely in the tube to prevent hair or anything else from being caught between the coils of the spring, even when the hook is engaged with the anchoring member farthest from the tube 6.

Figure 6:
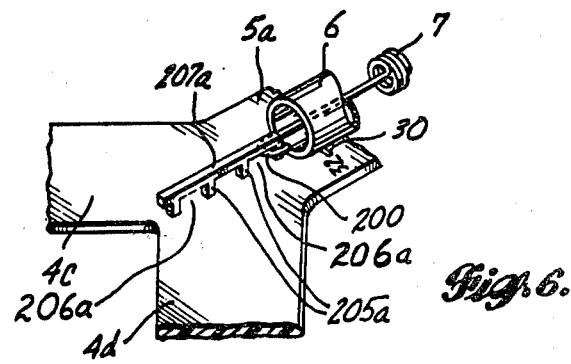
Figure 5:
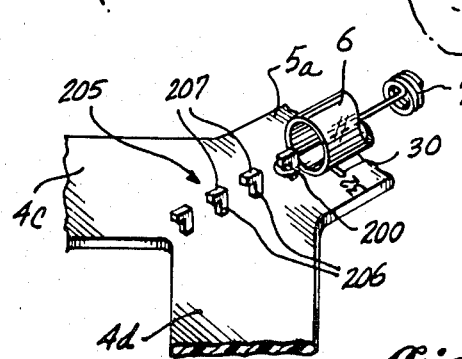

In the spring anchor means of FIG. 5, the hook-engageable anchor members are angle posts 205 having recesses 206 formed beneath caps shown as arms 207 projecting horizontally away from the spring 7. The spring hook 200 can be hooked around either side of the post shank into the recess 206 of any selected post depending upon the degree of force desired to be exerted by the force-producing unit. In FIG. 6, the posts 205a are integrally connected by a cap bar 207a connecting the upper ends of all the posts. The spring hook 200 can be hooked around any post 205a into a recess 206a as in FIG. 5.

Figure 7:
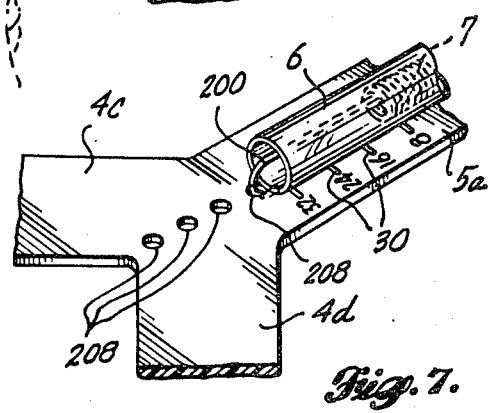

In FIG. 7, the hook-engageable anchor members are simply the rims of apertures 208 extending through the headcap at the junction of the strap sections 4c and 4d.

While the spring adjustments shown in FIGS. 2 to 7 achieve the desired result of allowing the orthodontist to quickly and precisely adjust the amount of force to be applied to the tie rod, it may be disadvantageous to be made so easily that it can be accomplished readily by a patient. The stress produced by force exerted on the patient's jaw and/or teeth during treatment can be quite uncomfortable. Therefore, uncooperative patients have themselves adjusted orthodontic appliances to relax the force to a level which is comfortable but much less effective for orthodontic treatment. Of course, the hook 200 of the springs shown in FIGS. 3 to 6 could be lengthened and, once the desired level of force determined, crimped around the anchor member with a pair of pliers. However, by such expedient the ease of adjusting the applied force is lost. Furthermore, a determined patient could uncrimp and move the hook and still defeat the purpose of the treatment.

The component connector of the orthodontic appliance shown in FIG. 8 includes a spring force adjustment which retains the ease of adjusting the force produced by spring 7 while deterring readjustment by the patient. The spring force adjustment includes an anchor member 10 carried by the backing 5a and having a plurality of integrally connected arches 11 and rectangular passages 12a, 12b extending through them. As best shown in FIGS. 11 and 12, passages 12a are chamfered at 13 opposite the spring 7 to enable easier engagement of hook 200 with the arches 11. The width of rectangular passage 12b closest to spring 7 is greater than the width of rectangular passages 12a, the purpose of which will be described later. The arches 11 also have cambered grooves 14 in the arch extrados. The spacing between the arches and the depth of the grooves are such that the hook 200 may be easily repositioned with a pair of needlenose pliers. It would be quite difficult to accomplish such repositioning without the use of such pliers.

Since the force exerted by the spring 7 in the various force-producing units described above can be altered to provide the desired force, it is preferred that there be calibration means to indicate the degree of force which is being produced by the spring in its different adjusted conditions. Such calibration means are shown in FIGS. 3, 5, 6, 7 and 10, as including a calibration scale 30 graduated in ounces, having lines corresponding to such graduations that in FIGS. 3, 5, 6 and 7 are visible through the transparent housing tube 6 for coordination with the end of the spring 7 remote from the side strap 8. The FIG. 10 scale is aligned with the arches 11 for coordination with the end of hook 200. Thus in FIGS. 3 and 7 the spring 7 is set to provide an average working pull of eight ounces and in FIG. 10 an average working pull of sixteen ounces.

Figure 15:
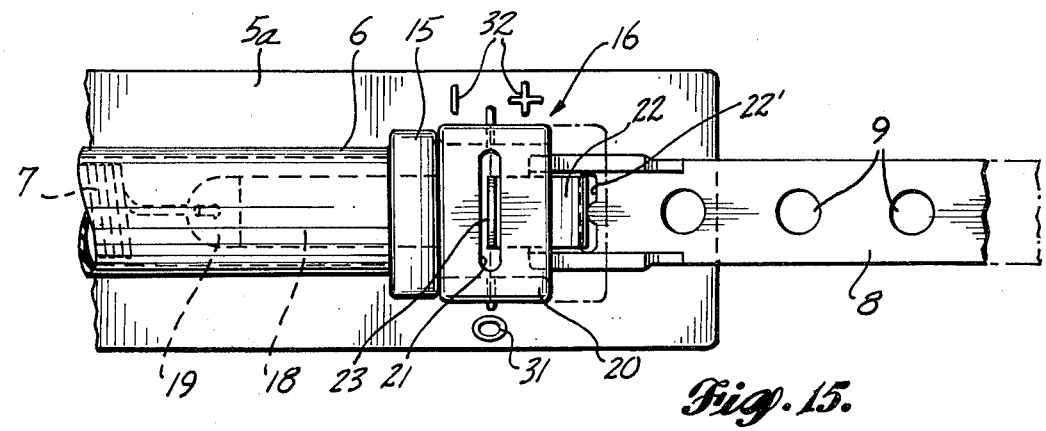
FIG. 15 is a plan of the disconnectible connection component, on the scale of FIG. 10 and having parts broken away.
Figure 16:
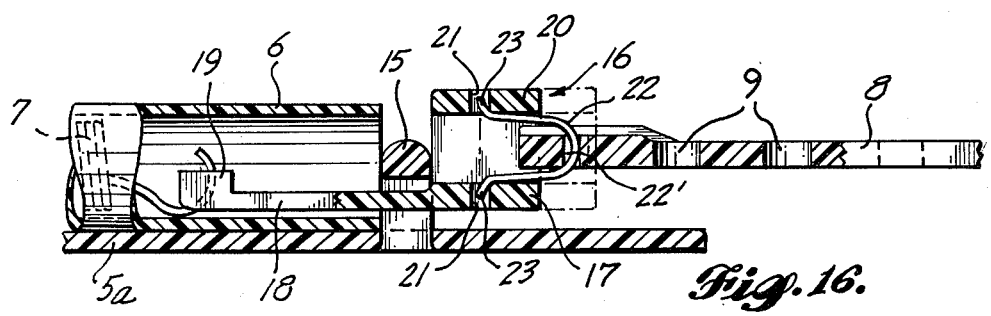
FIGS. 16 and 17 are longitudinal sections through the disconnectible connection component shown in FIG. 15, showing parts in different relationships.

Reference is made to the "average" working pull because considerable movement of the side strap 8 relative to the force-producing unit 3 occurs and the pull at one end of the working range will be different from the pull at the opposite end of the working range. Some range of movement is required to hook the tie rod 2 to the side strap 8. After such attachment, when the head and lower jaw are held in the most usual position the left end of the bridge 20 on intermediate strap 18 which connects spring 7 and side strap 8 should be aligned with the zero index mark 31, as shown in FIGS. 15 and 16 in broken lines. When the left end of the intermediate bridge is aligned with such index mark, the pull produced by the spring will be that designated by the calibration 30 aligned with the arch 11 with which the hook 200 on the left end of the spring is engaged. When the left end of bridge 20 moves to the left of the zero index mark 31 as shown in FIG. 15, the pull of the spring will be somewhat reduced, as indicated by the minus sign of the index 32. When the side strap 8 is pulled to draw the intermediate strap bridge to the right until its left end passes to the right beyond the zero index mark, as indicated by the plus sign in FIG. 15, for example, the pull produced by the spring will be greater than that indicated by the calibration 30 with which the left end of the spring is aligned in FIG. 3.

The width of the rectangular passage 12b of arch 11 adjacent to the spring 7 enables the top bevel end 6a of housing tube 6 to be engageable within the rectangular passage. As shown in FIGS. 8, 9, 11 and 14, the edges of the bevel engage the intrados of the arch and such engagement is maintained by the tube 6 being wedged between the anchor member 10 and the stop bridge 15. Therefore the tube is restrained from lateral displacement relative to the backing 5a in a simpler and more compact manner than is afforded by the use of the curved posts 29" shown in FIG. 3.

Further compactness over the embodiments shown in my prior U.S. Pat. No. 4,115,921 may be achieved by using the improved disconnectible connection 16 shown in FIGS. 8, 9 and 15 to 18. As explained above, it is desirable for the tie rod 2 and the head-engaging or neck-engaging force reaction band means, such as the FIG. 1 headcap 4, to be disconnected automatically in response to application of a pulling force to the tie rod exceeding a predetermined value, for example, seven pounds.

Disconnection between the tie rod 2 and the neckband or headcap preferably is accomplished by disconnecting the side strap 8 from the force-producing unit 3. Such a disconnectible connection 16 is shown in FIGS. 8 and 9 as including the widened end portion 17 of the intermediate strap 18 remote from the end of such strap carrying abutment 19. Such widened end portion, constituting one connection element, carries the bridge 20, located opposite such widened end portion of the connection element. The bridge and widened end portion of the connection element cooperate to form a box having opposite parallel sides which can receive within it the end portion of side strap 8 as shown in FIG. 9. The bridge 20 and widened end portion 17 have transverse slots 21 in the opposite parallel sides of the box.

Figure 17:
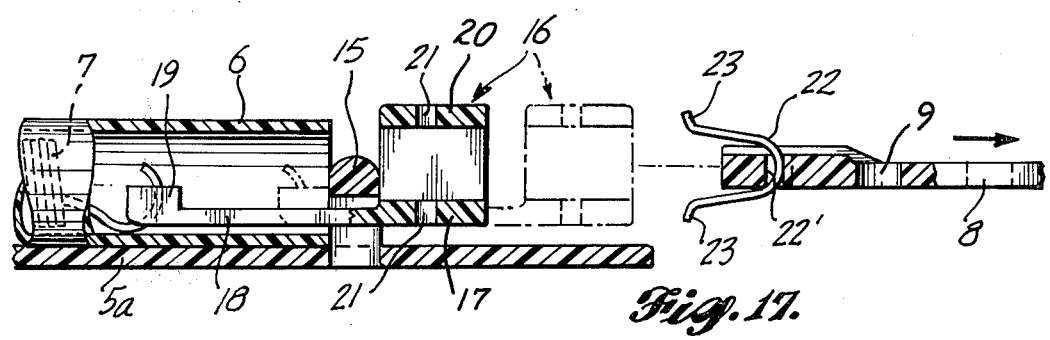

The end portion of the side strap 8 remote from the tie rod 2 carries a symmetrical U-shaped return-bent load-releasing spring strip 22, preferably of metal, forming a second connecting element. The central portion of such spring strip extends through a transverse slot 22' in the end portion of the side strap, as shown in FIGS. 15 and 16. Such spring strip includes outwardly bent hooked end portions 23 which are engageable in the respective slots 21 in the opposite sides of the box formed by bridge 20 and the widened end portion 17 of the intermediate strap 18. The side strap 8 is assembled with the intermediate strap 18 by threading the side strap over stop bridge 15 and beneath the left side of bridge 20 as seen in FIGS. 9, 16 and 17 and moving it from left to right until the hooked end portions 23 of spring strip 22 snap into slots 21.

The amount of pull required to be exerted on side strap 8 to disconnect the side strap from the intermediate strap should be greater than the pull exerted on the side strap 8 by spring 7 within the normal working range of the appliance. Thus a pull which will stretch spring 7 from the solid-line position of the intermediate strap 8 to the broken-line position of FIG. 17, in which the abutment 19 is engaged with the left side of bridge 15, will be insufficient to effect separation of the side strap 8 and intermediate strap 18. If a further pull is exerted on the side strap 8 to the right, the intermediate strap is restrained from being moved by the side strap 8 because of the engagement of abutment 19 with the left side of bridge 15.

The structure of the disconnectible connection is very precise, enabling the minimum tension and the amount of movement between side strap 8 and intermediate strap 18 which will effect disconnection of these strap members to be determined quite accurately. In order to be able to select most readily the predetermined minimum tension between strap 8 and strap 18 which will effect disconnection of the connection, it is preferred that the degree of such tension be determined almost entirely by the characteristics of the spring strip 22. Consequently, bridge 20 with which such strip cooperates is made of very rigid construction.

The proportions of the connection parts and the spring characteristics of the spring strip 22 should be quite exact so as to provide a prestressed condition of the spring when the connector parts have been assembled into the relationship shown in FIGS. 15 and 16. When the pull on side strap 8 exceeds a predetermined value, the hooked end portions 23 of the spring strip 22 are moved toward each other by wedging action on such hooked end portions of the slots 21 in the bridge 20 and in the widened end portion 17 so as to withdraw such end portions from the slots for disconnecting the side strap 8 from the intermediate strap 18 and enabling the side strap to be moved to the right away from the intermediate strap to the position of FIG. 17.

The extension movement of side strap 8 relative to intermediate strap 18 after the abutment 19 has engaged bridge 15 to release the hooked spring strip ends 23 from slots 21 is minimal, such as less than one millimeter. For the usual orthodontic treatment the pull exerted by spring 7 is in the range of eight to forty-eight ounces, that is, one-half a pound to three pounds. The spring 22 may have a preload of four pounds when the parts are in the position shown in FIG. 16, which means that a steady pull of four pounds applied to the side strap 8 will not shift that strap to the right relative to the intermediate strap 18.

The spring 22 may be selected so that a steady pull of five pounds applied to the side strap 8 will move such side strap relative to the intermediate strap to disconnect the connection. A sudden sharp pull of considerably less magnitude could also effect movement of the side strap 8 to the right from the position of FIG. 16 to disconnect the side strap from the intermediate strap. The spring 22 can be selected for disconnection of the parts under loads of different magnitude depending on the type of treatment for which the particular appliance is designed.

Figure 18:
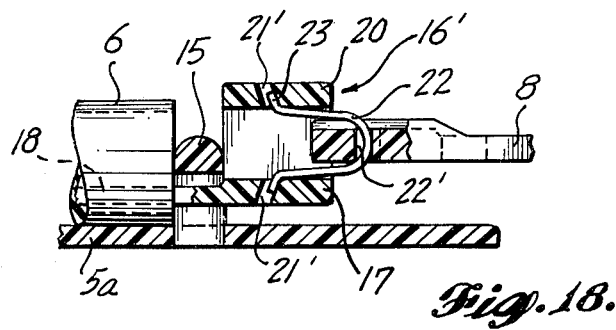
FIG. 18 is a longitudinal section through a modified disconnectible connection component.

The disconnectible connection 16' of FIG. 18 has the same general structure as the disconnectible connection shown in FIGS. 8, 9 and 15 to 17. The modification is that the transverse slots 21' are canted. Therefore the amount of pull required to disconnect the connector is less than that required in the FIG. 16 embodiment.

I claim:

1. In an orthodontic appliance including force-reaction means engageable with the wearer's head and/or neck, an orthodontic treatment force-applying device for applying a force to a jaw and resilient force-producing means connected between the force-reaction means and the force-applying device, the improvement comprising the force-producing means including a helical spring having a hook carried by one end thereof, and a plurality of arches carried by the appliance, arranged in a row aligned with said spring and selectively engageable by said hook for adjusting the degree of force produced by said spring.

2. In the appliance defined in claim 1, the anchor member arches being round arches.

3. In the appliance defined in claim 1, the anchor member arches being square arches.

4. In the appliance defined in claim 1, the anchor member arches being connected at the arch piers.

5. In the appliance defined in claim 1, the arches including a groove for receiving the hook.

6. In an orthodontic appliance including force-reaction means engageable with the wearer's head and/or neck, an orthodontic treatment force-applying device for applying a force to a jaw and resilient force-producing means connected between the force-reaction means and the force-applying device, the improvement comprising the force-producing means including a helical spring having a hook carried by one end thereof, and a plurality of posts carried by the appliance, arranged in a row aligned with said spring and selectively engageable by said hook for adjusting the degree of force produced by said spring.

7. In the appliance defined in claim 1, a spring housing tube having a beveled end engageable with an arch to deter movement of the tube relative to the force-reaction means.

8. In the appliance defined in claim 1, disconnectible connection means connected to the force-applying device and the force-producing means including two separable elements, a bridge carried by one of said elements and located opposite said one element, said bridge and said one element each having a slot, and a return-bent strip spring carried by the other of said elements, said spring incuding hooked-end portions engageable in said slots and movable beneath said bridge automatically in response to application between said two elements of a force exceeding a predetermined force.

9. In an orthodontic appliance including force-reaction means engageable with the wearer's head and/or neck, an orthodontic treatment force-applying device for applying force to a jaw connecting means connecting the force-reaction means and the force-applying device, a force-producing helical spring engaged between the force-reaction means and the force-applying device and a tube housing the spring, the improvement comprising the tube having a beveled end, and an arch carried by the connecting means and engageable by said beveled tube end to deter movement of the tube relative to the connecting means.

10. In an orthodontic appliance including force-reaction means engageable with the wearer's head and/or neck, an orthodontic force-applying device for applying force to a jaw, disconnectible connection means connected to the force-applying device, and a resilient force-producing unit connecting the force-reaction means and the disconnectible connection means for exerting a substantially linear force between such means tending to reduce the distance between such means, the improvement comprising the disconnectible connection means including two separable elements, a bridge carried by one of said elements and located opposite said one element for forming therewith a box with substantially parallel opposite sides, each such opposite side of said box having a slot, and a return-bent strip spring carried by the other of said elements, said spring including hooked-end portions receivable in said box, engageable respectively in said slots and movable out of said box automatically in response to application between said two elements of a force exceeding a predetermined force.

11. In the appliance defined in claim 10, the opposed slots being oppositely canted.

12. In the appliance defined in claim 6, the anchor members being angle posts.

13. In the appliance defined in claim 6, a cap bar connecting the upper ends of the posts.

* * * * *